United States Patent
Pan et al.

[19]

[11] Patent Number: 6,068,598

[45] Date of Patent: May 30, 2000

[54] METHOD AND APPARATUS FOR AUTOMATIC DOPPLER ANGLE ESTIMATION IN ULTRASOUND IMAGING

[75] Inventors: Lihong Pan, Brookfield; Michael J. Washburn, New Berlin; Larry Y. L. Mo, Waukesha, all of Wis.

[73] Assignee: General Electric Company, Milwaukee, Wis.

[21] Appl. No.: 09/201,982

[22] Filed: Dec. 1, 1998

[51] Int. Cl.[7] ........................................... A61B 8/02
[52] U.S. Cl. .......................................... 600/453; 600/454
[58] Field of Search .................................. 600/437, 441, 600/453–457; 73/625, 626, 861.25

[56] References Cited

U.S. PATENT DOCUMENTS 5,375,600  12/1994  Melton, Jr. et al. .................... 600/455
5,820,561  10/1998  Olstad et al. ........................... 600/453
5,941,826   8/1999  Goujon .................................. 600/451

*Primary Examiner*—Marvin M. Lateef
*Assistant Examiner*—Ali M. Imam
*Attorney, Agent, or Firm*—Dennis M. Flaherty; Christian G. Cabou; Phyllis Y. Price

[57] ABSTRACT

A method for automatic Doppler angle estimation based on the B-mode and color flow (if available) image. The method uses an algorithm for automatic vessel slope measurement which first finds an optimal initial point within the sample volume or range gate, and then searches for the most reliable pixel points (near or far walls) based on a combination of intensity-only and intensity-difference thresholds, before performing a slope estimation. B-mode intensity data and, optionally, color flow velocity or power data (before gray/color mapping) are used. The algorithm may also be applied to methods for automatic tracking of vessel diameter and flow rate calculations, although the primary objective is to achieve automatic Doppler angle estimation in an ultrasound scanner.

23 Claims, 4 Drawing Sheets

METHOD AND APPARATUS FOR AUTOMATIC DOPPLER ANGLE ESTIMATION IN ULTRASOUND IMAGING

FIELD OF THE INVENTION

This invention generally relates to the imaging of moving ultrasound scatterers. In particular, the invention relates to methods for determining the Doppler angle between an ultrasound beam and a blood vessel in medical diagnostic ultrasound imaging.

BACKGROUND OF THE INVENTION

Premium medical diagnostic ultrasound imaging systems require a comprehensive set of imaging modes. These are the major imaging modes used in clinical diagnosis and include timeline Doppler, color flow Doppler, B mode and M mode. In the B mode, such ultrasound imaging systems create two-dimensional images of tissue in which the brightness of a pixel is based on the intensity of the echo return. Alternatively, in a color flow imaging mode, the movement of fluid (e.g., blood) or tissue can be imaged. Measurement of blood flow in the heart and vessels using the Doppler effect is well known. The phase shift of backscattered ultrasound waves may be used to measure the velocity of the backscatterers from tissue or blood. The Doppler shift may be displayed using different colors to represent speed and direction of flow. In the spectral Doppler imaging mode, the power spectrum of these Doppler frequency shifts are computed for visual display as velocity-time waveforms.

one of the primary advantages of Doppler ultrasound is that it can provide noninvasive and quantitative measurements of blood flow in vessels. Given the angle θ between the insonifying beam and the flow axis (hereinafter referred to as the "Doppler angle"), the magnitude of the velocity vector can be determined by the standard Doppler equation:

$$v = c f_d / (2 f_0 \cos \theta) \quad (1)$$

where c is the speed of sound in blood, $f_0$ is the transmit frequency and $f_d$ is the motion-induced Doppler frequency shift in the backscattered ultrasound signal.

In conventional ultrasound scanners that perform B-mode and spectral Doppler imaging either simultaneously or in a segmented fashion, the angle between the Doppler beam cursor (beam centerline) and a vessel slope cursor in the B-mode image is used to convert Doppler frequency shifts into velocity units according to the Doppler equation. The operator is required to manually adjust (e.g., via a toggle switch) the vessel slope cursor based on the orientation of the vessel wall(s) in the B-mode image. The Doppler angle value is usually displayed along with the graphic. Since the Doppler angle adjustments are based on visual judgment, they are susceptible to error, especially if the angle step size is coarse. If fine angle adjustments are possible, the process can become time consuming. Therefore, an automatic method of adjusting the vessel slope cursor is needed to improve both the accuracy and efficiency of Doppler velocity measurements.

European Published Patent Application EP 0842638 teaches a method for automatically tracking the vessel walls, thereby enabling vessel diameter and volume flow measurements. However, the method requires the operator to first manually position the wall lines of a special cursor until they are coincident with the near and far vessel walls. In the middle of the special cursor lies the vessel slope line which is parallel to the wall lines.

U.S. Pat. No. 5,690,116 teaches a method for automatic measurement of the Doppler angle and an arrangement for carrying out the method. This method consists of the following basic steps: (1) From an initial point, a first isotropic tracing of rays over the region of interest is performed so as to provide a histogram of gray levels of selected points along the rays. (2) An image processing algorithm is executed on the histogram which results in a lower threshold for detecting vessel wall echoes. (3) A second tracing of rays from the initial point is performed, during which the gray level of each point of each ray is compared with the threshold, and the first end point of each ray whose gray level exceeds the threshold is classified as an edge point. This results in a representation of the blood vessel in the form of a so-called "local mark" of triangular sectors. (4) The slope of the regression line of the local mark is determined and the Doppler angle between the fitted line and the Doppler (beam) cursor is calculated. Since a linear regression of the coordinates of all the pixels in the local mark is performed, this prior art method implicitly assumes that the pixels representing the near and far vessel walls are both clear and reliable. The validity of the resultant slope estimate is tested by checking the coefficient of correlation. A correlation below a certain acceptable level (e.g., 0.5) is held to be indicative of poor positioning of the sectional plane, and the operator must make another attempt after correction.

In routine clinical examinations, even if the scan plane is aligned properly with the central axis of the vessel, often one of the two walls may be corrupted or masked by reverberation noise and/or shadows. Sometimes a nonlinear gray map is used to improve the perceived contrast of the image display. For these reasons, using a gray-level-only threshold alone can lead to false detection of edges. Furthermore, it is not uncommon that one of the two vessel walls will not appear clearly in the image simply because of the scan geometry in relation to the curvature of the vessel. In some cases the near and far walls may not even be parallel in the best vessel image that can be obtained in the time allowed. If a Doppler velocity measurement still needs to be carried out in any of the above situations, the user will often align the vessel slope cursor to the more clearly defined vessel wall, or make the best judgment by trying to "see through" some of the clutter in the vessel image. To automate the Doppler angle estimation in such challenging situations, a more robust method than that known in the prior art is needed.

SUMMARY OF THE INVENTION

The present invention is a method for automatic Doppler angle estimation based on the B-mode and color flow (if available) image. The method uses an algorithm for automatic vessel slope measurement which first finds an optimal initial point within the sample volume or range gate, and then searches for the most reliable pixel points (near or far wall) based on a combination of intensity-only and intensity-difference thresholds, before performing a slope estimation. B-mode intensity data and, optionally, color flow velocity or power data (before gray/color mapping) are used. The algorithm may also be applied to methods for automatic tracking of vessel diameter and flow rate calculations, although the primary objective is to achieve automatic Doppler angle estimation in an ultrasound scanner.

DETAILED DESCRIPTION OF THE PREFERRED EMBODIMENTS

Figure 1:
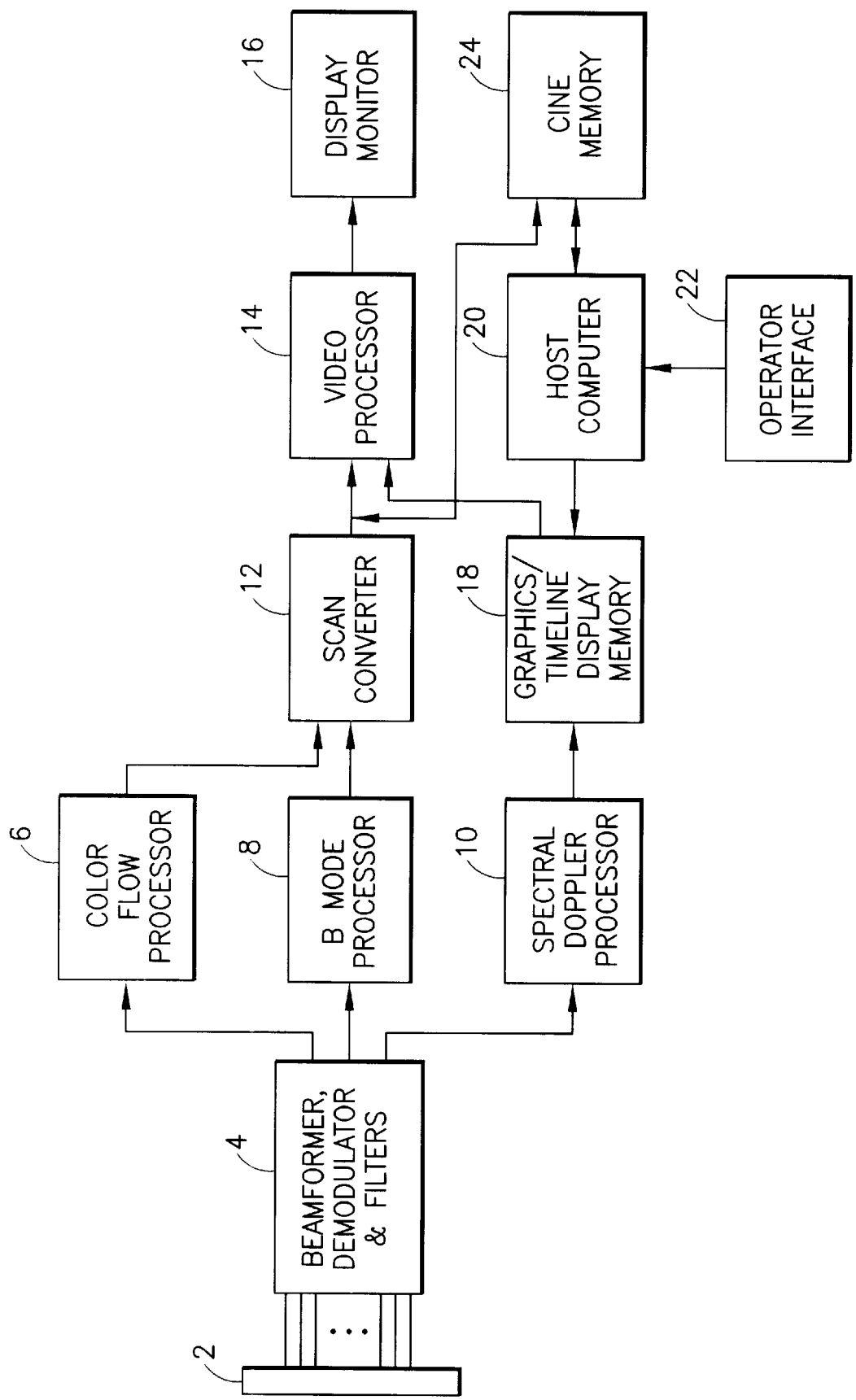
FIG. 1 is a schematic showing a block diagram of a general ultrasound imaging system which supports the preferred embodiments of the present invention.

One conventional ultrasound imaging system is generally depicted in FIG. 1. The main data path begins with the analog RF inputs to the beamformer board 4 from the transducer 2. The beamformer board 4 is responsible for the transmit and receive beamforming. The beamformer's signal inputs are the low-level analog RF signals from the transducer elements. The beamformer board 4, which comprises a beamformer, a demodulator and filters, outputs two summed digital baseband I and Q receive beams formed from acquired data samples. These data samples are derived from the reflected ultrasound from respective focal zones of the transmitted beams. The I and Q data is sent to FIR filters which are programmed with filter coefficients to pass a band of frequencies centered at the fundamental frequency $f_0$ of the transmit waveform or a (sub)harmonic frequency thereof.

The image data output from the filters is sent to the midprocessor subsystem, where it is processed according to the acquisition mode and output as processed vector data. Typically, the mid-processor subsystem comprises a color flow processor 6, a B-mode processor 8 and a spectral Doppler processor 10. Alternatively, a digital signal processor or array of such processors can be programmed to process signals for all three modes.

The B-mode processor 8 converts the baseband I and Q data from the beamformer board 4 into a log-compressed version of the signal envelope. The B-mode function images the time-varying amplitude of the envelope of the signal as a gray scale. The envelope of a baseband signal is the magnitude of the vector which I and Q represent. The I,Q phase angle is not used in the B-mode display. The magnitude of the signal is the square root of the sum of the squares of the orthogonal components, i.e., $(I^2+Q^2)^{1/2}$. The B-mode intensity data is output to a B-mode acoustic line memory (not shown) in the scan converter 12.

The scan converter 12 accepts the processed B-mode vector data, interpolates where necessary, and converts the data into X-Y format for video display. The scan-converted frames are passed to a video processor 14, which maps the video data to a gray-scale mapping for video display. A conventional ultrasound imaging system typically employs a variety of gray maps, which are simple transfer functions of the raw image data to display gray levels. The gray-scale image frames are then sent to the display monitor 16 for display.

The B-mode images displayed by monitor 16 are produced from an image frame of data in which each datum indicates the intensity or brightness of a respective pixel in the display. An image frame may, e.g., comprise a 256×256 data array in which each intensity datum is an 8-bit binary number that indicates pixel brightness. Each pixel has an intensity value which is a function of the backscatter cross section of a respective sample volume in response to interrogating ultrasonic pulses and the gray map employed. The displayed image represents the tissue and/or blood flow in a plane through the body being imaged.

The color flow processor 6 is used to provide a real-time two-dimensional image of blood velocity in the imaging plane. The frequency of sound waves reflecting from the inside of blood vessels, heart cavities, etc. is shifted in proportion to the velocity of the blood cells: positively shifted for cells moving towards the transducer and negatively for those moving away. The blood velocity is calculated by measuring the phase shift from firing to firing at a specific range gate. Instead of measuring the Doppler spectrum at one range gate in the image, mean blood velocity from multiple vector positions and multiple range gates along each vector are calculated, and a two-dimensional image is made from this information. The color flow processor 6 receives the summed left and right, complex I/Q data from the beamformer board 4 and processes it to calculate the mean blood velocity, variance (representing blood turbulence) and total prenormalization power for all sample volumes within an operator-defined region. These three output values are then combined into two final outputs, one primary and one secondary. The primary output will be either velocity or power. The secondary output can be either variance or power. Which two values will be displayed is determined by the operator-selected display mode. Both values are sent to an color acoustic line memory (not shown) in the scan converter 12. The change or shift in backscattered frequency increases when blood flows toward the transducer and decreases when blood flows away from the transducer. Typically, color flow mode displays hundreds of adjacent sample volumes simultaneously, all laid over a B-mode image and color-coded to represent each sample volume's velocity.

In the color flow mode of the conventional ultrasound imaging system being described here, an ultrasound transducer array is activated to transmit a series of multi-cycle (typically 4–8 cycles) tone bursts which are focused at the same transmit focal position with the same transmit characteristics. These tone bursts are fired at a pulse repetition frequency (PRF). The PRF is typically in the kilo-hertz range. A series of transmit firings focused at the same transmit focal position are referred to as a "packet". Each transmit beam propagates through the object being scanned and is reflected by ultrasound scatterers such as blood cells. The return signals are detected by the elements of the transducer array and then formed into a receive beam by a beamformer.

For example, the traditional color firing sequence is a series of firings (e.g., tone bursts) along the same position, which firings produce the respective receive signals:

$F_1\ F_2\ F_3\ F_4\ \ldots\ F_M$ where $F_i$ is the receive signal for the i-th firing and M is the number of firings in a packet. These receive signals are loaded into a corner turner memory, and a high pass filter (wall filter) is applied to each down range position across firings, i.e., in "slow time". In the simplest case of a (1, −1) wall filter, each range point is filtered to produce the respective difference signals:

$(F_1-F_2)(F_2-F_3)(F_3-F_4)\ \ldots\ (F_{M-1}-F_M)$ and these differences are input to a color flow velocity estimator. Typically, the corner turner memory, wall filter and parameter (e.g., velocity) estimators are incorporated into the color flow processor 6.

The color and B-mode acoustic line memories in scan converter 12 respectively accept processed digital data from the color flow and B-mode processors. These components of the scan converter also perform the coordinate transformation of the color flow and B-mode data from polar coordinate (R-θ) sector format or Cartesian coordinate linear format to appropriately scaled Cartesian coordinate display pixel data, which is stored in an X-Y display memory (not shown) in the scan converter. Color flow images are produced by superimposing a color image of the velocity of moving material, such as blood, over a black and white anatomical B-mode image.

If the image to be displayed is a combination of one B-mode frame and one color flow frame, then both frames are passed to the video processor 14, which maps the B-mode data to a gray map and maps the color flow data to a color map for video display. In the final displayed image, the color pixel data is super-imposed on the gray-scale pixel data. Successive frames of color flow and/or B-mode data are stored in a cine memory 24 on a first-in, first-out basis. Storage can be continuous or as a result of an external trigger event. The cine memory 24 is like a circular image buffer that runs in the background, capturing image data that is displayed in real time to the user. When the user freezes the system (by operation of an appropriate device on the operator interface 22), the user has the capability to view image data previously captured in cine memory.

In spectral Doppler imaging, the I/Q components are integrated (summed) over a specific time interval and then sampled by the spectral Doppler processor 10. The summing interval and the transmit burst length together define the length of the sample volume as specified by the user. A "sum and dump" operation effectively yields the Doppler signal backscattered from the sample volume. The Doppler signal is passed through a wall filter which rejects any clutter in the signal corresponding to stationary or very slow-moving tissue. The filtered output is then fed into a spectrum analyzer, which typically takes Fast Fourier Transforms (FFTs) over a moving time window of 32 to 128 samples. Each FFT power spectrum is compressed and then output by the spectral Doppler processor 10 to a graphics/timeline display memory 18. The video processor 14 maps the compressed spectral Doppler data to a gray scale for display on the monitor 16 as a single spectral line at a particular time point in the Doppler velocity (frequency) versus time spectrogram.

System control is centered in a host computer (i.e., master controller) 20, which accepts operator inputs through an operator interface 22 (e.g., a control panel) and in turn controls the various subsystems. The host computer 20 performs system level control functions. It accepts inputs from the operator via the operator interface 22 as well as system status changes (e.g., mode changes) and makes appropriate system changes. A system control bus (not shown) provides the interface from the host computer to the subsystems. A scan controller provides real-time (acoustic vector rate) control inputs to the various subsystems. The scan controller is programmed by the host computer with the vector sequences and synchronization options for acoustic frame acquisitions. Thus, the scan controller controls the beam distribution and the beam density. The scan controller transmits the beam parameters defined by the host computer to the subsystems via a scan control bus (not shown).

The conventional system has the capability to superimpose graphical symbols on any ultrasound image. The superimposition of graphics on the image frame is accomplished in the video processor 14, which receives the ultrasound image frame from the X-Y display memory in the scan converter 12 and the graphics data from graphics/timeline display memory 18. The graphics data is processed and input into the graphics/timeline display memory 18 by the host computer 20 or, alternatively, by a graphics processor which is synchronized with the other subsystems by the host computer.

Figure 5:
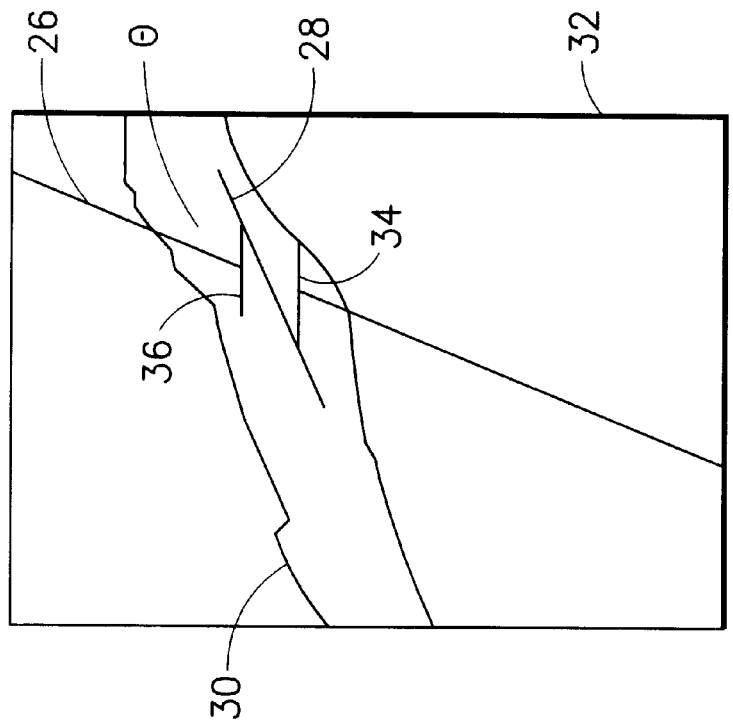
FIG. 5 is a schematic depicting the ultrasound image of FIG. 2 with a Doppler beam cursor and a vessel slope cursor superimposed thereon.

In accordance with the present invention, the Doppler angle is estimated automatically by the host computer. The estimated Doppler angle value is then used by the host computer to estimate the flow velocity as a function of the Doppler frequency shift. Referring to FIG. 5, the angle between a Doppler beam cursor (beam centerline) 26 and a vessel slope cursor 28 on a vessel 30 in the B-mode image 32 is used to convert Doppler frequency shifts into velocity units according to the Doppler equation. The Doppler angle value is usually displayed along with the graphic.

Figure 2:
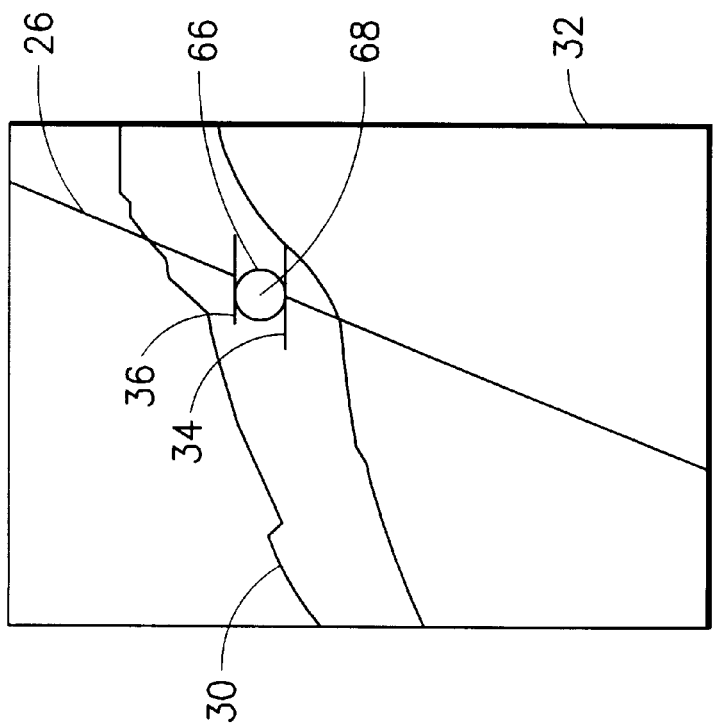
FIG. 2 is a schematic depicting an ultrasound image of a portion of a blood vessel with a Doppler beam cursor superimposed thereon.

To accomplish the foregoing, the user requests an automatic Doppler angle estimation by pressing a rotary knob on the operator interface 22 (see FIG. 1) after the user has placed the Doppler range gate (sample volume) graphic, consisting of a range gate top graphic 36 and a range gate bottom graphic 34, on the vessel 30 in the image 32, as seen in FIG. 2, also via the operator interface. If the image is not frozen at the time of the user request, the host computer automatically freezes the image (step 38 in FIG. 6) and stores the frame of imaging data into cine memory. Once the image is frozen, the frame of B and color flow (if available) image data are read from the cine memory by the host computer (step 40 in FIG. 6). Based on the image data, a Doppler angle is computed, and the Doppler angle value and graphic are updated. If the image was automatically forced into a frozen state as described above, the image is unfrozen. If the user is not satisfied with the automatically estimated Doppler angle, the user can adjust the vessel slope cursor by dialing the rotary knob that he pressed to initiate the automatic Doppler angle estimation. (The automatic freezing of the image is not necessary if the image data can be obtained while live scanning continues.)

Figure 6:
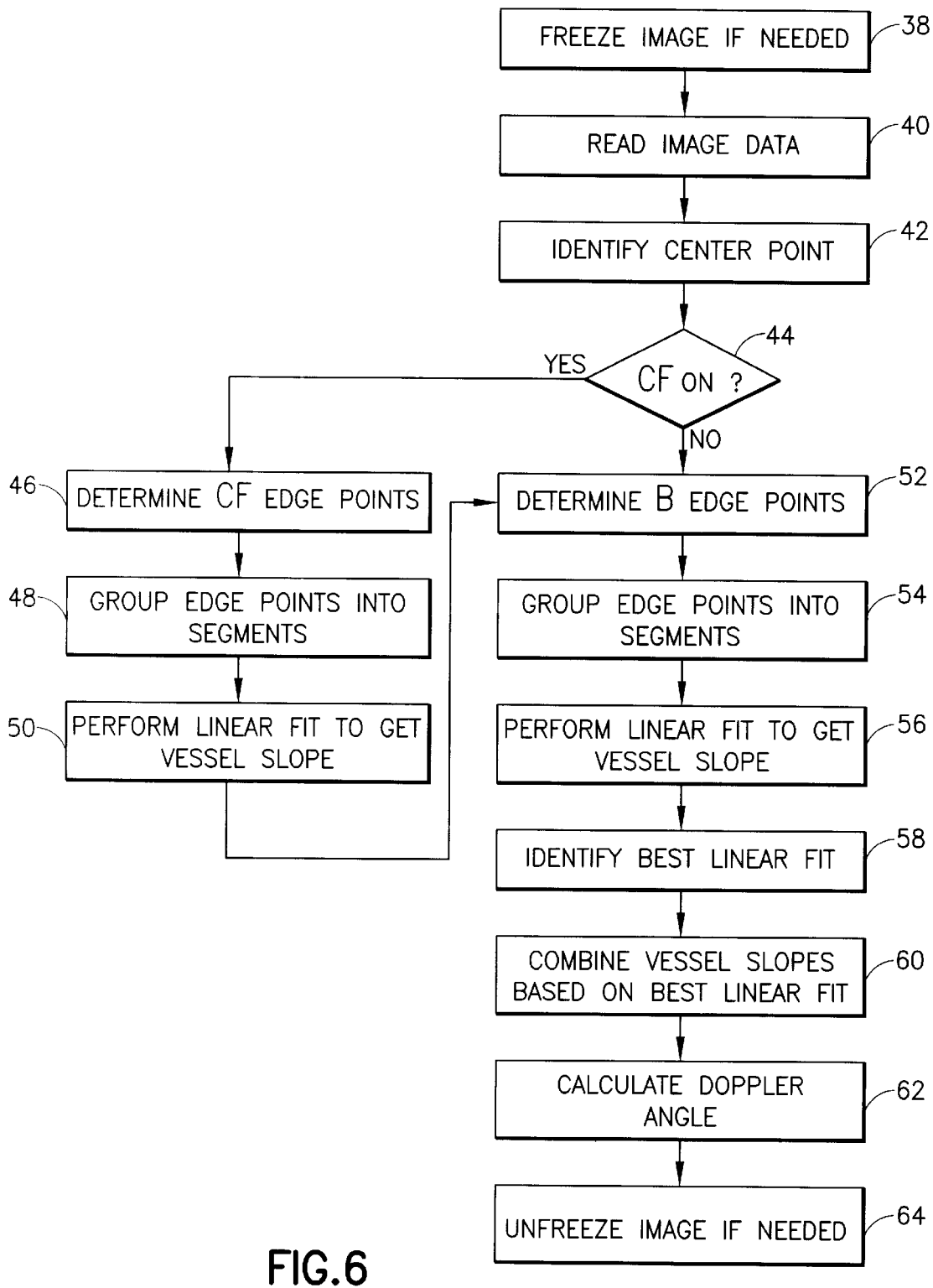
FIG. 6 is a flowchart depicting the algorithm for automatically adjusting the vessel slope cursor in accordance with the preferred embodiment of the invention.

To automatically compute a Doppler angle, the host computer performs the algorithm shown in FIG. 6 on the frame of image data read from cine memory in step 40. A center point of a search area is identified in step 42 as follows. If the average of a number of B-mode intensity values in a small area 66 about the center point 68 of the Doppler range gate (see FIG. 2) is at or below some threshold, then that location is used as the center point of the searching algorithm. If the B-mode intensity values are above the threshold, then the host computer searches outward from that point by ½ the total range gate width in all directions to determine the area with the minimum average B-mode intensity values (typical of scattering from blood). If that minimum-average-intensity area is below the intensity at the original center point area by some percentage, then the center point is moved to the center 70 of this minimum area, as seen in FIG. 3.

Figure 3:
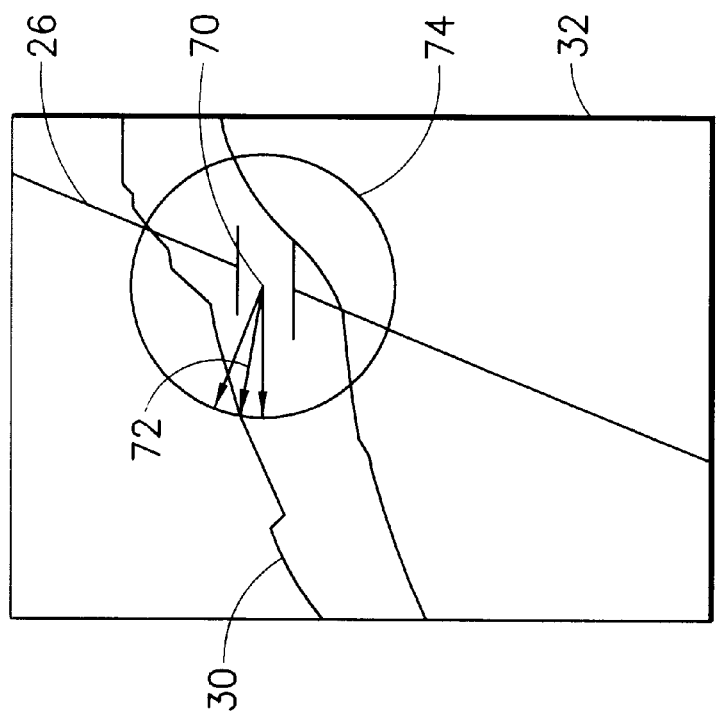
FIG. 3 is a schematic depicting the ultrasound image of FIG. 2 with edge point search information in accordance with the preferred embodiment of the invention superimposed thereon.

The host computer then determines (step 44 in FIG. 6) whether the image frame read from cine memory includes color flow data at pixel addresses corresponding to the location of the center point 70 (see FIG. 3). If the image frame includes color flow data corresponding to the center point, then the host computer searches out from the center point 70 along radial lines 72 which are angularly spaced S degrees apart over an entire 360° range, as shown in FIG. 3. The distance to search from the center is D cm. This edge search area is indicated by circle 74 in FIG. 3.

Figure 4:
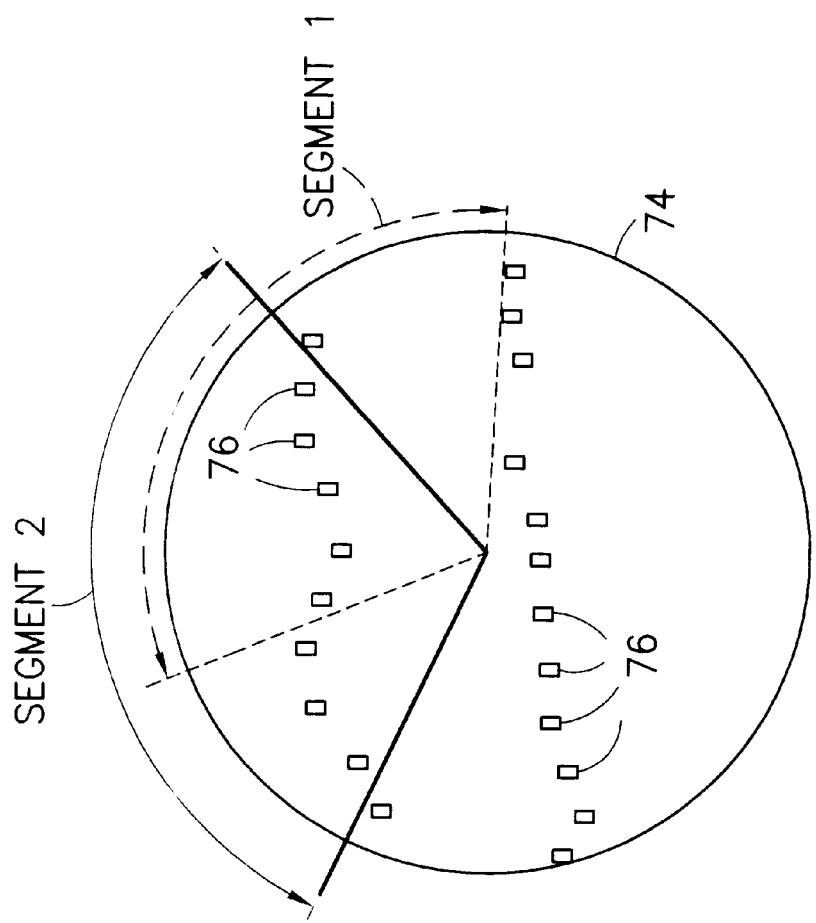
FIG. 4 is a schematic depicting segmentation of the edge points in accordance with the preferred embodiment of the invention.

Along each radial line 72, the host computer searches from the center point 70 and stores the point as an edge point if it is the first of X (≧2) points displaying B-mode intensity data instead of color flow velocity or power data (step 46 in FIG. 6). Exemplary edge points are depicted as rectangles 76 in FIG. 4. If no such point is found before searching D cm or finding the edge of the color region of interest, then no edge point is marked along that radial line. Once each radial line is searched, all the edge points 76 in a certain segment of the edge point search area (e.g., Segment 1 indicated by dotted lines in FIG. 4) are grouped together (step 48) and fed to a line-fit algorithm which generates both a vessel slope estimate and a goodness-of-fit measurement (step 50). This is repeated for other segments (e.g., Segment 2 indicated by solid straight lines in FIG. 4) and in each case the slope of the vessel and the goodness of fit are recorded. The segments may overlap each other by some number of degrees, as do Segments 1 and 2 shown in FIG. 4. If a particular segment does not have some minimum number of edge points within it, then that segment is disregarded.

In addition to the foregoing, the algorithm also determines B-mode edge points (step 52) by searching the B-mode intensity data from the center point in radial lines spaced S degrees apart over an entire 360° range. The distance to search from the center is D cm. Along each radial line each B-mode intensity value (corresponding to respective pixels) is replaced with the average of itself and its two neighbors along the radius. The peak and minimum intensities along the averaged radial line as well as the largest difference (from one pixel to the next) are each recorded. If the difference between the peak and minimum intensities does not exceed some threshold, then no edge point is specified for this ray. If the difference between the peak and minimum intensities exceeds the threshold, then a search is started at some number of points from the center and stops when a point (the edge point) is found to exceed a difference-only threshold, an intensity-only threshold or a combined difference and intensity threshold. For example, if the pixel location is 50% of the maximum intensity and 30% of the maximum difference, then it would pass the combined difference and intensity threshold. The intensity at the edge point is noted. If no such point is found before searching D cm or finding the edge of the B-mode image, then no edge point is marked along that radial line. Once each radial line has been searched, some percent of the edge points are disregarded. The disregarded edge points are those associated with the lowest intensities. All of the remaining edge points in a certain segment of the edge point search area are grouped (step 54) and then fed to a line-fit algorithm which generates both a vessel slope estimate and a goodness-of-fit measurement (step 54). This is repeated for other segments, and in each case the vessel slope and the goodness of fit are recorded. The segments may overlap each other by some number of degrees. If a particular segment does not have some minimum number of edge points within it, then that segment is disregarded.

If no B-mode or color flow mode segment generated enough edge points to get a vessel slope estimate, the distance D is increased and the algorithm is rerun. (If rerunning the algorithm still results in no vessel slope estimates, then the Doppler angle remains unchanged.)

At this point in the algorithm, estimates of the vessel slope and their corresponding goodness-of-fit measurements are known for some number of segments (for B mode and possibly color flow mode). The segment having the best goodness of fit is identified (step 58) and its vessel slope is combined (averaged) with all the other vessel slope estimates that have a goodness of fit measurement not exceeding some difference relative to the best one (step 60). However, if color is active and the best color vessel slope exceeds some number of degrees (indicating a vessel somewhat vertical), then only color data is used in this vessel slope-combining algorithm. This is done because somewhat vertical vessel walls are difficult to detect in B-mode due to the lateral smearing of the image data. On the other hand, if color is not active, steps 46, 48 and 50 in FIG. 6 are not performed and step 60 combines only vessel slopes derived from B-mode edge points.

The host computer determines the Doppler angle by calculating (step 62 in FIG. 6) the angle between the combined vessel slope 28 and the Doppler beam cursor 26, as shown in FIG. 5. Referring to FIG. 1, the host computer 20 then uses the calculated Doppler angle value to compute the velocity in accordance with the Doppler equation. If necessary, the image is then unfrozen (step 64 in FIG. 6).

The foregoing preferred embodiments have been disclosed for the purpose of illustration. Variations and modifications of the concept of the invention will be readily apparent to persons skilled in the art. For example, although along each radial line each B-mode intensity value (corresponding to respective pixels) can be replaced with the average of itself and its two neighbors along the radius, any suitable smoothing filter which reduces statistical variations can be used. All such variations and modifications are intended to be encompassed by the claims set forth hereinafter.

We claim:

1. A method for estimating a Doppler angle between a direction of an ultrasound transmit beam and an axis of a blood vessel, comprising the steps of:

displaying an ultrasound image of said blood vessel;

storing a frame of image parameter values from which said ultrasound image was derived, said image parameter values corresponding to respective pixels in said image;

placing a graphic representing a range gate overlying said blood vessel in said image;

identifying a center point of a search area corresponding to a point lying within said range gate, wherein the image parameter values in said frame corresponding to pixels in a center area surrounding said center point have a lower average image parameter value than the image parameter values in said frame corresponding to pixels in other areas within said search area;

searching for a respective edge point outward along each one of a multiplicity of radial lines extending from said center point and angularly spaced over a predetermined angular range within said search area, said searches being conducted from said center point to a predetermined distance along each radial line in accordance with a search algorithm;

applying a line-fit algorithm to at least some of the edge points within each of a plurality of segments of said search area, said line-fit algorithm generating respective pluralities of vessel slope estimates and goodness-of-fit measurements;

identifying a best goodness-of-fit measurement from amongst said plurality of goodness-of-fit measurements;

combining the vessel slope estimate corresponding to said best goodness-of-fit measurement with other vessel slope estimates corresponding to other goodness-of-fit measurements not exceeding some difference relative to said best goodness-of-fit measurement; and determining said Doppler angle as a function of said combined vessel slope and said transmit beam direction.

2. The method as recited in claim 1, wherein said combining step comprises averaging said vessel slope estimate corresponding to said best goodness-of-fit measurement with said other vessel slope estimates.

3. The method as recited in claim 1, further comprising the steps, performed after said searching step and prior to said applying step, of:

storing a respective image parameter value for each edge point; and discarding edge points corresponding to image parameter values below a predetermined threshold.

4. The method as recited in claim 1, wherein said image parameter values comprise B-mode intensity values for at least some of said pixels.

5. The method as recited in claim 4, wherein said image parameter values further comprise color flow estimates for pixels in said frame other than said pixels having B-mode intensity values.

6. The method as recited in claim 4, wherein said search algorithm comprises the steps of:

along each radial line, applying a smoothing filter to reduce statistical variations;

for each filtered radial line, storing the peak and minimum image parameter values and the largest difference between image parameter values corresponding to adjacent pixels;

if a difference between said peak and minimum image parameter values for each averaged radial line exceeds a predetermined threshold, searching for a point along each radial line having an image parameter value which satisfies at least one of a difference criterion and a value criterion; and identifying said point as an edge point.

7. The method as recited in claim 5, wherein said search algorithm comprises the steps of:

along each radial line, searching for a point which is the first of X points having B-mode intensity values instead of color flow estimates; and identifying said point as an edge point.

8. A system comprising:

a display device comprising a multiplicity of pixels energized to display an ultrasound image of a blood vessel with a graphic representing a range gate overlying said blood vessel;

a memory for storing a frame of image parameter values corresponding to respective pixels of said an ultrasound image;

a computer programmed to perform the steps of:

(a) identifying a center point of a search area corresponding to a point lying within said range gate, wherein the image parameter values in said frame corresponding to pixels in a center area surrounding said center point have a lower average image parameter value than the image parameter values in said frame corresponding to pixels in other areas within said search area;

(b) searching for a respective edge point outward along each one of a multiplicity of radial lines extending from said center point and angularly spaced over a predetermined angular range within said search area, said searches being conducted from said center point to a predetermined distance along each radial line in accordance with a search algorithm;

(c) applying a line-fit algorithm to at least some of the edge points within each of a plurality of segments of said search area, said line-fit algorithm generating respective pluralities of vessel slope estimates and goodness-of-fit measurements;

(d) identifying a best goodness-of-fit measurement from amongst said plurality of goodness-of-fit measurements;

(e) combining the vessel slope estimate corresponding to said best goodness-of-fit measurement with other vessel slope estimates corresponding to other goodness-of-fit measurements not exceeding some difference relative to said best goodness-of-fit measurement; and (f) determining said Doppler angle as a function of said combined vessel slope and said transmit beam direction.

9. The system as recited in claim 8, wherein said combining step comprises averaging said vessel slope estimate corresponding to said best goodness-of-fit measurement with said other vessel slope estimates.

10. The system as recited in claim 8, wherein said computer is further programmed to perform, after said searching step and prior to said applying step, the steps of:

storing a respective image parameter value for each edge point; and discarding edge points corresponding to image parameter values below a predetermined threshold.

11. The system as recited in claim 8, wherein said image parameter values comprise B-mode intensity values for at least some of said pixels.

12. The system as recited in claim 11, wherein said image parameter values further comprise color flow estimates for pixels in said frame other than said pixels having B-mode intensity values.

13. The system as recited in claim 11, wherein said search algorithm comprises the steps of:

along each radial line, replacing each image parameter value by the average of itself and the two image parameter values corresponding to the adjacent pixels;

for each averaged radial line, storing the peak and minimum image parameter values and the largest difference between image parameter values corresponding to adjacent pixels;

if a difference between said peak and minimum image parameter values for each averaged radial line exceeds a predetermined threshold, searching for a point along each radial line having an image parameter value which satisfies at least one of a difference criterion and a value criterion; and identifying said point as an edge point.

14. The system as recited in claim 12, wherein said search algorithm comprises the steps of:

along each radial line, searching for a point which is the first of X points having B-mode intensity values instead of color flow estimates; and identifying said point as an edge point.

15. The system as recited in claim 8, further comprising:

an ultrasound transducer array comprising a multiplicity of transducer elements;

a transmit beamformer for pulsing selected transducer elements to transmit a series of ultrasound transmit beams in a scan plane;

a receive beamformer coupled to selected transducer elements of said transducer array for acquiring respective receive signals subsequent to respective beam transmits;

a signal processor for forming vectors of image parameter values from said receive signals;

a scan converter for converting said vectors into a frame of image parameter values and storing said frame of image parameter values in said memory; and a video processor comprising a gray-scale mapping for mapping said frame of image parameter values retrieved from said memory into gray-scale pixel values.

16. A system for automatically estimating a Doppler angle between a direction of an ultrasound transmit beam and an axis of a blood vessel, comprising:

means for displaying an ultrasound image of said blood vessel;

means for storing a frame of image parameter values from which said ultrasound image was derived, said image parameter values corresponding to respective pixels in said image;

means for placing a graphic representing a range gate overlying said blood vessel in said image;

means for identifying a center point of a search area corresponding to a point lying within said range gate, wherein the image parameter values in said frame corresponding to pixels in a center area surrounding said center point have a lower average image parameter value than the image parameter values in said frame corresponding to pixels in other areas within said search area;

means for searching for a respective edge point outward along each one of a multiplicity of radial lines extending from said center point and angularly spaced over a predetermined angular range within said search area, said searches being conducted from said center point to a predetermined distance along each radial line in accordance with a search algorithm;

means for applying a line-fit algorithm to at least some of the edge points within each of a plurality of segments of said search area, said line-fit algorithm generating respective pluralities of vessel slope estimates and goodness-of-fit measurements;

means for identifying a best goodness-of-fit measurement from amongst said plurality of goodness-of-fit measurements;

means for combining the vessel slope estimate corresponding to said best goodness-of-fit measurement with other vessel slope estimates corresponding to other goodness-of-fit measurements not exceeding some difference relative to said best goodness-of-fit measurement; and means for determining said Doppler angle as a function of said combined vessel slope and said transmit beam direction.

17. The system as recited in claim 16, wherein said combining means comprise means for averaging said vessel slope estimate corresponding to said best goodness-of-fit measurement with said other vessel slope estimates.

18. An ultrasound imaging system comprising:

an ultrasound transducer array comprising a multiplicity of transducer elements;

a transmit beamformer for pulsing selected transducer elements to transmit a series of ultrasound transmit beams in a scan plane;

a receive beamformer coupled to selected transducer elements of said transducer array for acquiring respective receive signals subsequent to respective beam transmits;

a signal processor for forming vectors of image parameter values from said receive signals;

a scan converter for converting said vectors into a frame of image parameter values;

a video processor comprising a gray-scale mapping for mapping said frame of image parameter values into gray-scale pixel values;

a display device comprising a multiplicity of pixels for displaying pixel values from said video processor; and a computer programmed to estimate a Doppler angle between a direction of one of said ultrasound transmit beams and an axis of a blood vessel by performing an algorithm on a subset of the image parameter values of said frame.

19. A system comprising:

a display device comprising a multiplicity of pixels energized to display an ultrasound image of a blood vessel with a graphic representing a range gate overlying said blood vessel;

a memory for storing a frame of image parameter values corresponding to respective pixels of said an ultrasound image; and a computer programmed to estimate a Doppler angle between a direction of one of said ultrasound transmit beams and an axis of a blood vessel by performing an algorithm on a subset of the image parameter values of said frame.

20. The system as recited in claim 19, wherein said image parameter values comprise B-mode intensity values for at least some of said pixels.

21. The system as recited in claim 20, wherein said image parameter values further comprise color flow estimates for pixels in said frame other than said pixels having B-mode intensity values.

22. A method comprising the steps of:

acquiring a set of ultrasound vector data derived from ultrasound scattering in a scan plane intersecting a blood vessel;

processing said set of ultrasound vector data to form a frame of image parameter values;

gray-scale mapping said frame of image parameter values into gray-scale pixel values;

displaying an ultrasound image of said blood vessel comprising said gray-scale pixel values;

storing said frame of image parameter values;

placing a graphic representing a range gate over-lying said blood vessel in said displayed image;

identifying a center point of a search area corresponding to a point lying within said range gate, wherein the image parameter values in said frame corresponding to pixels in a center area surrounding said center point have a lower average image parameter value than the image parameter values in said frame corresponding to pixels in other areas within said search area; and estimating a slope of said blood vessel by performing an algorithm on the image parameter values of said frame corresponding to pixels within said search area.

23. A system comprising:

means for acquiring a set of ultrasound vector data derived from ultrasound scattering in a scan plane intersecting a blood vessel;

a signal processor for processing said set of ultrasound vector data to form a frame of image parameter values;

a video processor for gray-scale mapping said frame of image parameter values into gray-scale pixel values;

a display device for displaying an ultrasound image of said blood vessel comprising said gray-scale pixel values;

a memory for storing said frame of image parameter values;

means for placing a graphic representing a range gate overlying said blood vessel in said displayed image;

means for identifying a center point of a search area corresponding to a point lying within said range gate, wherein the image parameter values in said frame corresponding to pixels in a center area surrounding said center point have a lower average image parameter value than the image parameter values in said frame corresponding to pixels in other areas within said search area; and means for estimating a slope of said blood vessel by performing an algorithm on the image parameter values of said frame corresponding to pixels within said search area.

* * * * *